(12) United States Patent
Thomas et al.

(10) Patent No.: US 12,023,146 B2
(45) Date of Patent: Jul. 2, 2024

(54) MULTI-MODAL LUNG CAPACITY MEASUREMENT FOR RESPIRATORY ILLNESS PREDICTION

(71) Applicant: International Business Machines Corporation, Armonk, NY (US)

(72) Inventors: Samuel Thomas, White Plains, NY (US); Nalini K. Ratha, Yorktown Heights, NY (US); Jonathan Hudson Connell, II, Cortlandt-Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 363 days.

(21) Appl. No.: 17/065,936

(22) Filed: Oct. 8, 2020

(65) Prior Publication Data
US 2022/0110542 A1    Apr. 14, 2022

(51) Int. Cl.
| | | |
|---|---|---|
| *A61B 5/091* | (2006.01) | |
| *A61B 5/00* | (2006.01) | |
| *G06N 3/08* | (2023.01) | |

(52) U.S. Cl.
CPC ............ *A61B 5/091* (2013.01); *A61B 5/0022* (2013.01); *A61B 5/7275* (2013.01); *A61B 5/749* (2013.01); *G06N 3/08* (2013.01)

(58) Field of Classification Search
CPC ..... A61B 5/0823; A61B 5/091; A61B 5/4803; A61B 5/7282; A61B 7/003; A61B 5/7275; G10L 25/66; G10L 15/25
See application file for complete search history.

(56) References Cited

U.S. PATENT DOCUMENTS

| | | |
|---|---|---|
| 2011/0125044 A1 | 5/2011 | Rhee et al. |
| 2011/0257971 A1 | 10/2011 | Morrison |
| | (Continued) | |

FOREIGN PATENT DOCUMENTS

| | | |
|---|---|---|
| CN | 107440721 A | 12/2017 |
| CN | 108135485 A | 6/2018 |
| | (Continued) | |

OTHER PUBLICATIONS

Reply to United Kingdom Examination Report dated Jun. 30, 2022 received in Application No. GB2113651.0, 7 pages.
(Continued)

*Primary Examiner* — Devin B Henson
*Assistant Examiner* — Jonathan M Haney
(74) *Attorney, Agent, or Firm* — Scully, Scott, Murphy & Presser, P.C.; Daniel P. Morris

(57) ABSTRACT

Determining lung capacity of includes capturing an audio waveform of the user performing an utterance presented to a user. A video of the user performing the utterance can be captured. The captured audio waveform and the video are analyzed for compliance. Based on the audio waveform, an indicator of respiratory function is determined. The indicator is compared with a reference indicator to determine health of the user. A machine learning model such as neural network can be trained to predict the indicator of the respiratory function based on input features comprising audio spectral and temporal characteristics of utterances. Determining the indicator or respiratory function can include running the trained machine learning model.

16 Claims, 11 Drawing Sheets

(56) References Cited

U.S. PATENT DOCUMENTS

| | | | |
|---|---|---|---|
| 2014/0114208 A1* | 4/2014 | Smith | A61P 27/02 600/558 |
| 2016/0081611 A1 | 3/2016 | Hampton et al. | |
| 2018/0158450 A1 | 6/2018 | Tokiwa et al. | |
| 2018/0240535 A1 | 8/2018 | Harper et al. | |
| 2019/0080803 A1 | 3/2019 | Lotan et al. | |
| 2019/0150879 A1 | 5/2019 | De Waele et al. | |
| 2019/0298271 A1* | 10/2019 | Zigel | A61B 5/4818 |
| 2019/0313919 A1 | 10/2019 | Pritchard et al. | |
| 2020/0098384 A1 | 3/2020 | Nematihosseinabadi et al. | |
| 2020/0118583 A1* | 4/2020 | Shallom | A61B 5/4803 |
| 2020/0151516 A1 | 5/2020 | Anushiravani et al. | |
| 2021/0153772 A1* | 5/2021 | Venneti | A61B 5/091 |
| 2021/0298711 A1 | 9/2021 | Miri et al. | |
| 2023/0045078 A1* | 2/2023 | Berisha | A61B 5/4803 |

FOREIGN PATENT DOCUMENTS

| | | |
|---|---|---|
| EP | 3637433 A1 | 4/2020 |
| WO | 2013057637 A1 | 4/2013 |
| WO | 2013059823 A1 | 4/2013 |
| WO | 2014037843 A1 | 3/2014 |
| WO | 2014045257 A1 | 3/2014 |
| WO | 2017068582 A1 | 4/2017 |

OTHER PUBLICATIONS

Nallanthighal, V.S., et al., "Deep Sensing of Breathing Signal during Conversational Speech" Interspeech 2019, Sep. 15-19, 2019, pp. 4110-4114.

Baese-Berk, M.M., et al., "Speaking rate consistency in native and non-native speakers of English", The Journal of the Acoustical Society of America, Accepted Aug. 12, 2015, Published Online Sep. 4, 2015, https://asa.scitation.org/doi/10.1121/1.492962, Accessed on Oct. 8, 2020, pp. EL223-EL228, vol. 138.

Elliott, T.M., et al., "The Modulation Transfer Function for Speech Intelligibility", PLoS Computational Biology, e1000302, Accepted Jan. 23, 2009, Published Mar. 6, 2009, https://journals.plos.prg/ploscompbiol/article?id=10.1371/journal.pcbi.1000302, Accessed Oct. 8, 2020, pp. 1-14, vol. 5, Issue 3.

Nyu, "Breathe for science", https://www.breatheforscience.com/?fbclid=IwAR1s3JnKKVjfvay3YMhkd29RSfDyGg85ZISKtdORsqEGjcJiaJ5dcPUgfls, Accessed on Oct. 8, 2020, 4 pages.

Singh, R., "Profiling Humans from their Voice", http://www.cs.haifa.ac.il/~orrd/BioCourse/Rita.pdf, Feb. 12, 2020, Accessed on Oct. 8, 2020, 122 pages.

Huber, J.E., "Effects of Utterance Length and Vocal Loudness on Speech Breathing in Older Adults", Respir Physiol Neurobiol, Author Manuscript, Published online Aug. 28, 2008, https://www.ncbi.nlm.nih.gov/pmc/articles/PMC2636560/, Accessed Oct. 8, 2020, 24 pages.

Palmeira, A.C., et al., "Use of the technique of counting numbers as a predictor of slow vital capacity in hospitalized individuals", Rev. CEFAC Sao Paulo Mar./Apr. 2015, vol. 17, No. 2, http://www.scielo.br/scielo.php?bid=S1516-18462015000200559&script=sci_arttext&tlng=en, Accessed on Oct. 8, 2020, pp. 559-566.

NCVS, "Lung Pressure and Power: A Potpourri of Topics", The National Center for Voice and Speech, Tutorials—Voice Production, Chapter 3: Fluid Flow in Respiratory Airways (Breathing), http://www.ncvs.org/ncvs/tutorials/voiceprod/tutorial/lung.html, Accessed on Oct. 8, 2020, 2 pages.

Wikipedia, "Vowel", https://en.wikipedia.org/wiki/Vowel, Last edited Oct. 6, 2020, Accessed on Oct. 8, 2020, 14 pages.

Wikipedia, "Nasal consonant", https://en.wikipedia.org/wiki/Nasal_consonant, Last edited on Jul. 19, 2020, Accessed on Oct. 8, 2020, 6 pages.

Wikipedia, "Speech tempo", https://en.wikipedia.org/wiki/Speech_tempo, Last edited Jun. 5, 2020, Accessed on Oct. 8, 2020, 4 pages.

Russell, K., "Identifying sounds in spectrograms", University of Manitoba, https://home.cc.umanitoba.ca/~krussll/phonetics/acoustic/spectrogram-sounds.html, Last modified Nov. 27, 2005, Accessed on Oct. 8, 2020, 6 pages.

Kelion, L., Coronavirus: Covid-19 detecting apps face teething problems, BBC News, https://www.bbc.com/news/technology-52215290, Apr. 8, 2020, Accessed on Oct. 8, 2020, 5 pages.

Carfagno, J., "AI-Powered Smart Stethoscope Revolutionizing Remote Medicine", DocWire News, https://www.docwirenews.com/docwire-pick/ai-powered-smart-stethoscope-revolutionizing-remote-medicine/, Jul. 10, 2019, Accessed on Oct. 8, 2020, 6 pages.

Dormehl, L., "Breakthrough A.I.-powered stethoscope diagnoses pneumonia like a robot doctor ", https://www.digitaltrends.com/cool-tech/johns hopkins-smart-stethoscope-ai/, Feb. 5, 2019, Accessed on Oct. 8, 2020, 4 pages.

NIST, "NIST Cloud Computing Program", http://csrc.nist.gov/groups/SNS/cloud-computing/index.html, Created Dec. 1, 2016, Updated Oct. 6, 2017, 9 pages.

Abushakra, A., et al., "Lung capacity estimation through acoustic signal of breath", Bioinformatics & Bioengineering (BIBE), Nov. 11-13, 2012, pp. 386-391.

United Kingdom Examination Report dated May 18, 2022 received in Application No. GB2113651.0, 20 pages.

United Kingdom Examination Report dated Nov. 28, 2022 received in Application No. GB2113651.0, 5 pages.

Reply to United Kingdom Examination Report dated Mar. 30, 2023 received in UK Application No. 2113651.0, 11 pages.

German Office Action dated Nov. 6, 2023 received in Application No. 10 2021 123 127.2, 14 pages.

* cited by examiner

MULTI-MODAL LUNG CAPACITY MEASUREMENT FOR RESPIRATORY ILLNESS PREDICTION

BACKGROUND

The present application relates generally to computers and computer applications, and more particularly to multimedia and speech processing for wellness detection.

Respiratory illness often impacts lungs slowly and is detected as the impact becomes severe. Lung capacity for air holding decreases slowly as the illness impacts the body. While early detection of the change in lung capacity can be useful, the current methodologies such as X-ray and CT scans require special set up and experts to analyze the scans. Those methodologies, for example, can be expensive, and not readily available.

BRIEF SUMMARY

A method and system for multi-modal lung capacity measurement for respiratory illness prediction can be provided. The method, in one aspect, can include presenting to a user a specification of an utterance to be performed. The method can also include capturing an audio waveform of the user performing the utterance. The method can further include capturing a video of the user performing the utterance. The method can also include analyzing the captured audio waveform and the video for compliance with the specification. The method can also include, based on the audio waveform, determining an indicator of respiratory function. The method can also include comparing the indicator with a reference indicator to determine health of the user.

A system, in one aspect, can include a processor and a memory coupled with the processor. The processor can be configured to present to a user a specification of an utterance to be performed. The processor can also be configured to capture an audio waveform of the user performing the utterance. The processor can also be configured to capture a video of the user performing the utterance. The processor can also be configured to analyze the captured audio waveform and the video for compliance with the specification. The processor can also be configured to, based on the audio waveform, determine an indicator of respiratory function. The processor can also be configured to compare the indicator with a reference indicator to determine health of the user.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Systems and methods are disclosed for determining lung capacity, for example, for respiratory illness prediction. In one or more embodiments, the systems and/or methods determine lung capacity based on multimedia analysis, e.g., speech processing and video processing. For example, the systems and/or methods may utilize protocols which correlate speech utterance characteristics with vital lung capacity. In an aspect, a simple, low cost and usable application on a user device such as on a mobile device can help users to self-check their progression. Allowing a user to reliably self-assess the user's lung capacity may expand the scope of testing both in terms of population and frequency.

In an aspect, the systems and methods may use the production of various classes of speech sounds as indicators of the wellness or health of an individual's respiratory system. For example, vowels are sounds produced when air from the lungs passes through the mouth with minimal obstruction and without audible friction. As air flows from the lungs, the vocal cords vibrate to produce these sounds. Given that these sounds (e.g., /a/ /e/ /i/ /o/ /u/) are produced as air is forced out from the lungs, the ability to produce a continuous, sustained vowel sound as example can be used as a measure of lung capacity. When the lungs are infected and/or are filled with fluid such as mucus there is a reduction in lung capacity, which in turn affects an individual's ability to produce a sustained vowel sound. Infection of the vocal tracts can also have an effect on the production of these sounds. As another example, nasal sounds are consonants produced when air is allowed to flow through the nasal cavity. When a sustained nasal like /m/ is produced with the mouth closed, it can be used as an indicator of how congested the nasal cavity is.

Human speech can be characterized from other vocalizations by distinct characteristics. For example, the typical speaking rate of English can be generalized to 4 syllables per second. Anomalies in speech characteristics may be perceived as abnormal and can be used as indicators of an individual's respiratory health.

Figure 1:
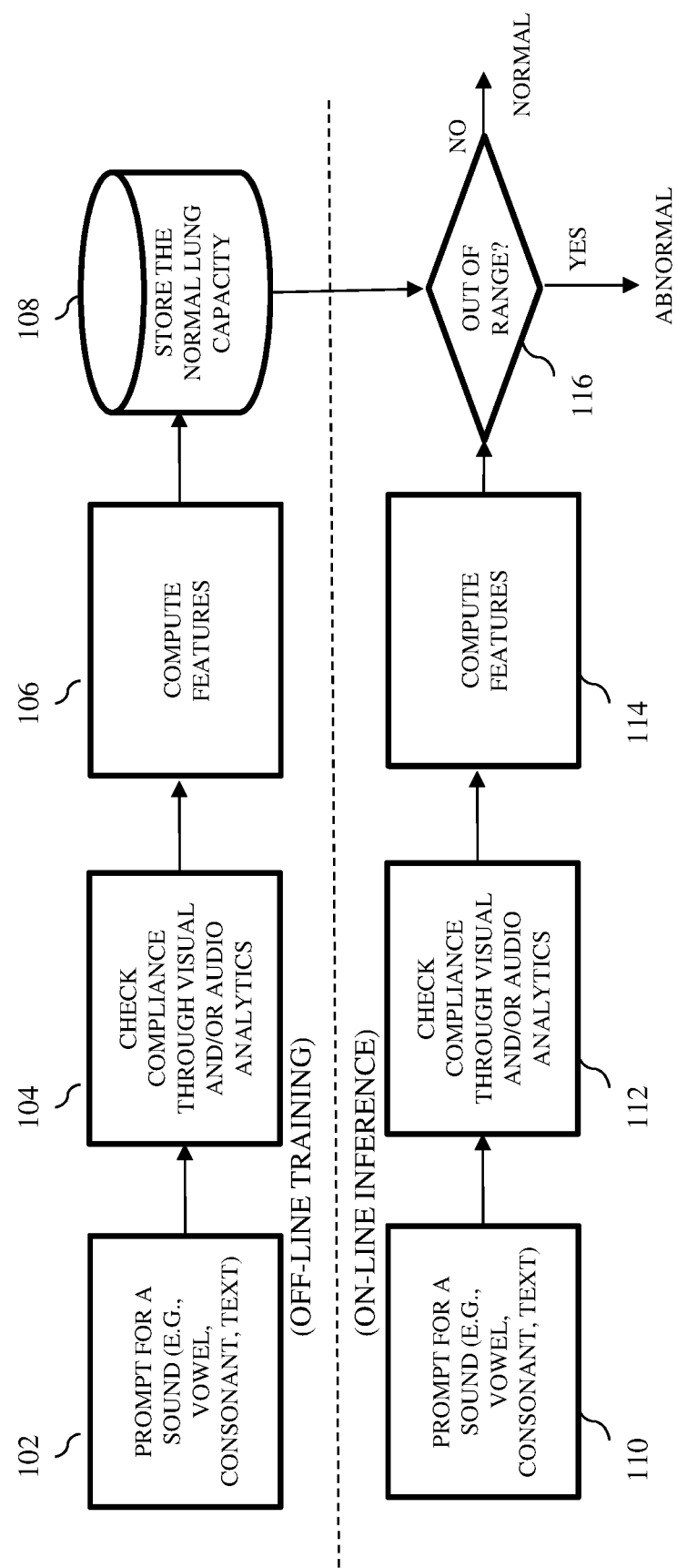
FIG. 1 is a diagram illustrating an overview of multimodal lung capacity determination for detecting possible respiratory illness in an embodiment.

FIG. 1 is a diagram illustrating an overview of multimodal lung capacity determination for detecting possible respiratory illness in an embodiment. The components shown in FIG. 1 can be implemented or run on a device or computer, for example, having one or more processors such as one or more hardware processors. A device or computer, for example, can be a mobile device running an application (e.g., mobile app), or another device. One or more hardware processors, for example, may include components such as programmable logic devices, microcontrollers, memory devices, and/or other hardware components, which may be configured to perform respective tasks described in the present disclosure. Coupled memory devices may be configured to selectively store instructions executable by one or more hardware processors.

A processor may be a central processing unit (CPU), a graphics processing unit (GPU), a field programmable gate array (FPGA), an application specific integrated circuit (ASIC), another suitable processing component or device, or one or more combinations thereof. The processor may be coupled with a memory device. The memory device may include random access memory (RAM), read-only memory (ROM) or another memory device, and may store data and/or processor instructions for implementing various functionalities associated with the methods and/or systems described herein. The processor may execute computer instructions stored in the memory or received from another computer device or medium.

At 102, a processor (e.g., running an application or running processor instructions) prompts a user to utter a sequence of sounds while holding one's breath. Uttering a sequence of sounds, for example, can include uttering vowels such as "a-e-i-o-u" (or vowels in any other order) a number of time until the user is out of breath. Other examples can include uttering consonants, words, reading a given text, and/or others. The methodology can also work with any other natural languages, and sounds having similar effects as vowels, consonants and other words.

At 104, a processor may check for compliance in the user's uttering of the sounds. For example, the processor may automatically and/or autonomously check for any discrepancies or errors made while the user is making the sound, which may affect accurately measuring the lung capacity. In this processing, the processor may use video analytics and/or audio analytics to determine compliance. For instance, the methodology in an embodiment can detect rushing through the making sounds such is counts in an uttering, for example, "1234567 . . . " versus (vs.) "1 2 3 4 5 6 7 . . . " Such rushed count can result in less air being used for each number, and may distort maximum count, which can be used as a measure. In an embodiment, the methodology may examine intensity envelope of sounds to determine and compensate for pacing. As another example, clipped or elongated words (e.g., "oone twoo threeee foour . . . " or "w'n tu tree fur . . . ") can result in variable amount of air being used for each vowel segment and variable utterance duration, which may distort measurement. In an embodiment, the methodology may directly measure vowel length from spectrogram to provide feedback. As yet another example, mumbling or partial whispering (e.g., "un tu 'ree fo . . . " or "whuun tuuu threeeh . . . ") can result in a less than normal volume of exhalation being expended. In an embodiment, the methodology may analyze signal-to-noise of vowel formants to reject utterance.

Image processing of the video captured while the user is making or uttering the sound can be analyzed for compliance. For example, images captured of the user while making the sound can detect whether the user is making proper facial, mouth and/or lip movements in uttering the sounds, is in a proper posture, etc., to be able to provide proper standard basis for making measurements, e.g., so as not to distort the measurements of the sound features being computed. For example, image processing of the video can establish identity continuity from video and establish that the data from the same user is being tested or trained. The processor captures the sounds made by the user, e.g., within compliance of making such sounds. If any discrepancies are detected while the user is providing the utterance, the processor asks that the user to re-utter or try again.

At 106, a processor may compute features associated with captured sounds. For example, the processor may analyze the sounds and compute various characteristics of the sounds as uttered by the user. The processor may also determine or obtain lung capacity measurement of the user, which correlates to the computed features or characteristics. Considering that the user made the sounds while in a healthy condition (e.g., "normal" condition of the lungs), the obtained lung capacity measurement (or measurement range) is then associated with "normal" lung capacity or "healthy" lung capacity of the user. In an embodiment, determining the user's lung capacity can include running a trained machine learning model such as a neural network model with the computed features as input features to the trained machine learning model. The machine learning model outputs the lung capacity measurement (or measurement range) corresponding to the input features.

Classes of sounds can include vowels and consonants. Such sounds exhibit distinct spectral signatures that can be used to identify them in spectrograms of speech. Vowels have distinct formant frequencies; Consonants have energy bursts in distinct frequency bands. Distinct spectro-temporal patterns can be observed in the modulation spectrum of speech. So, for example, features or characteristics can include, but are not limited to spectro-temporal characteristics such as speaking rate.

At 108, a processor may store the computed characteristics and the lung capacity measurement. The stored information can be used as a baseline or a reference point. Using such baseline, a processor may determine or assess normality or abnormality of the lung capacity, for example, at a different or later time.

Processing at 102, 104, 106 and 108 can be referred to as calibration processing or scaling. For instance, such processing can calibrate an individual's baseline or reference point for assessing respiratory or lung health, and can be specific to a particular individual.

In another aspect, the baseline calibration processing (e.g., shown at 102, 104, 106 and 108) can be performed for a general population group, for example, having common characteristics such as demographic and/or physical characteristics. For example, sample sounds from a group of users or individuals can be captured and the corresponding lung capacity measurement (or a range of measurements can be obtained, for example, by running a trained machine learning model. The obtained measurement can be used as a baseline (e.g., "normal" lung capacity at the group's healthy stage) for that group.

Processing at 110, 112, 114 and 116 can be performed to determine a user or individual's lung capacity at a given time (e.g., current time). At 110, a processor (e.g., running an application or running processor instructions) prompts a user to utter or repeat uttering a sequence of sounds. For instance, the user may be prompted to inhale then start speaking or uttering a sequence of sounds. Uttering a sequence of sounds, for example, can include uttering vowels such as "a-e-i-o-u" (or vowels in any other order) a number of time, e.g., until the user is out of breath. Other examples can include uttering consonants, words, reading a given text, and/or others. For instance, the user can be prompted to utter similar sounds as done during the baseline determination, for example, at 102.

At 112, a processor checks for compliance while the user is making the sound, for example, as done at 104, for example, using at least video analytics.

At 114, a processor computes features or characteristics associated with the user's uttering of the sounds. Based on the computed features, the processor may determine the lung capacity, e.g., the current lung capacity of the user. Determining the lung capacity may include running a trained machine learning model. The trained machine learning model can be the same model used to determine the baseline of the user or the group of users.

At 116, a processor compares the current lung capacity with the baseline capacity, for example, stored at 108, and determines whether the current lung capacity is out of range of the baseline capacity. If the current lung capacity is out of range, the processor determines that current capacity deviates from the normal range, and therefore may signal respiratory illness.

In an aspect, the machine learning model can be a neural network model or another machine learning model, which can be trained to predict lung capacity measurement, given a set of features or characteristics associated with utterances of a user. For example, training data for the machine learning model or neural network model can include labeled data which include characteristics of the sounds uttered by the user correlated to lung capacity measurements.

For instance, a neural network can be trained with input features as sound characteristics and output as the lung capacity measurement data. The parameters (e.g., weights and bias) of the neural network can be optimized to correlate the input sound features and the output lung capacity measurements. Briefly, an artificial neural network or neural network is a machine learning model, which can be trained to predict or classify an input data. An artificial neural network can include a succession of layers of neurons, which are interconnected so that output signals of neurons in one layer are weighted and transmitted to neurons in the next layer. A neuron Ni in a given layer may be connected to one or more neurons Nj in the next layer, and different weights wij can be associated with each neuron-neuron connection Ni-Nj for weighting signals transmitted from Ni to Nj. A neuron Nj generates output signals dependent on its accumulated inputs, and weighted signals can be propagated over successive layers of the network from an input to an output neuron layer. An artificial neural network machine learning model can undergo a training phase in which the sets of weights associated with respective neuron layers are determined. The network is exposed to a set of training data, in an iterative training scheme in which the weights are repeatedly updated as the network "learns" from the training data. The resulting trained model, with weights defined via the training operation, can be applied to perform a task based on new data.

In an embodiment, a self-calibration processing may include the following. Using a mobile phone or another device running an app, a user can be prompted to provide a "normal" measurement of the lung capacity by uttering "a", "e", "i", "o" and "u" (or another utterance) a number of times until the user is out of breath. Using this utterance characteristic, a baseline model of the lung air capacity is created (e.g., mean time and variance across normal samples). The above step can be repeated and averaged over a period of time in a period (e.g., in a week) to calibrate the "normal" state. The user may be asked to read a paragraph that fits on a screen of the device being used. From the sound signals, the modulation spectrum may be computed to estimate speaking rate baseline. During the testing phase, the user can be prompted to utter the vowels until the user is breathless, and a processor of the user's device may record the user making the utterance. The difference in the time averaged over the vowels from the calibrated baseline can signal an onset of respiratory illness. For instance, if the difference is above a threshold, the processor may signal that the lung capacity may not be normal. In another aspect, the user may be asked to read a paragraph of text displayed on a screen of the user's device. A processor of the user's device may compute the modulation spectrum to estimate the user's speaking rate. The processor may compare this speaking rate with the baseline speaking rate. If the deviation or difference is greater than a threshold, the processor may signal a loss of lung capacity.

Figure 2:
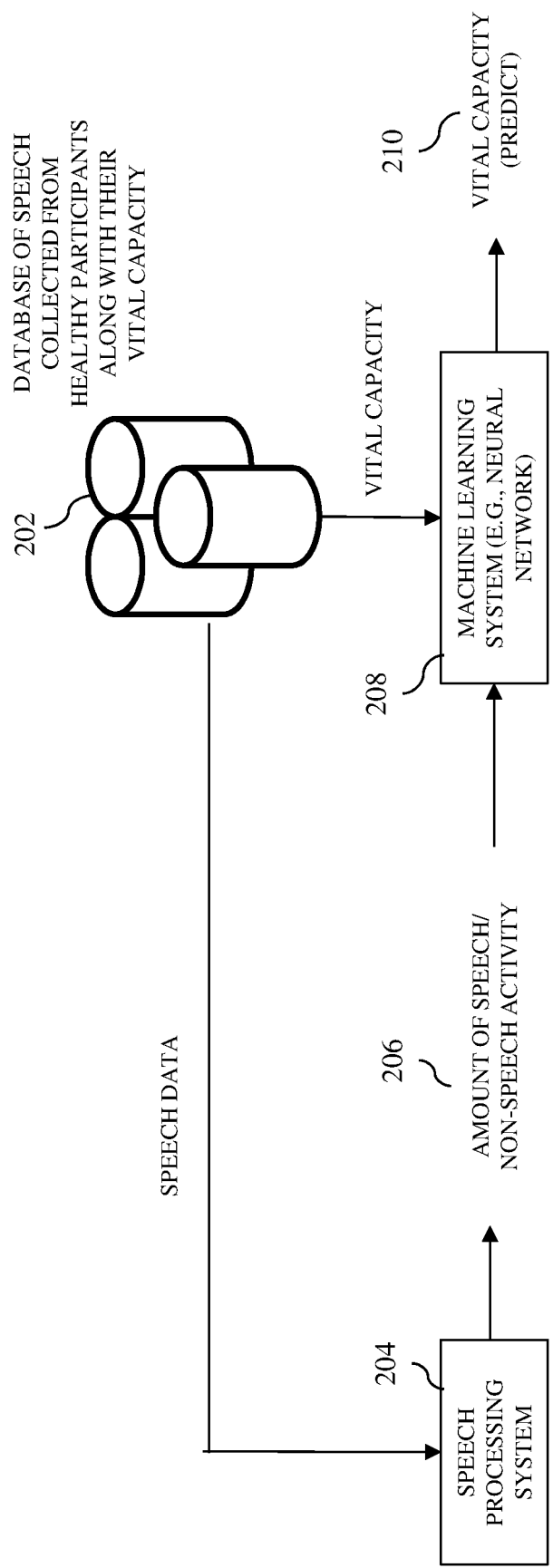
FIG. 2 illustrates training of a machine learning model to predict lung capacity in an embodiment.

FIG. 2 illustrates training of a machine learning model to predict lung capacity in an embodiment. Database of speech recordings 202 can include data representing speech recordings of a plurality of individuals. For example, an individual can be asked to inspire as much air as possible and during exhalation begin uttering speech sounds, for example, vowel and/or consonants in isolation or continuous speech. The individuals can be asked to repeat the uttering of such sounds, for example, for a number of times, for a period of time, or for example, while the individual can comfortably so do. For each of the subjects or individuals who have provided their recordings, their lung capacity is also measured. The recordings and associated measured lung capacity can be stored as a database 202 in one or more storage devices or systems.

At 204, the stored user speech is processed to extract or compute features or characteristics of the user speech. Extracted characteristics can include characteristics related to amounts of speech/non-speech activity 206. For instance, data such as spectral features, modulation frequency and joint spectro-temporal features can be extracted or computed from the speech recordings.

At 208, using the features or characteristics and associated lung capacity data, a machine learning model, for example, a neural network model can be trained to predict lung capacity. For example, the features and the associated lung capacity data are used as training data to optimize or train the parameters (e.g., weights and biases) of a neural network or another machine learning model. The trained neural network (or another machine learning model) then can be used to predict lung capacity 210, given a new set of features, which for example, the neural network has not seen before.

Figure 3:
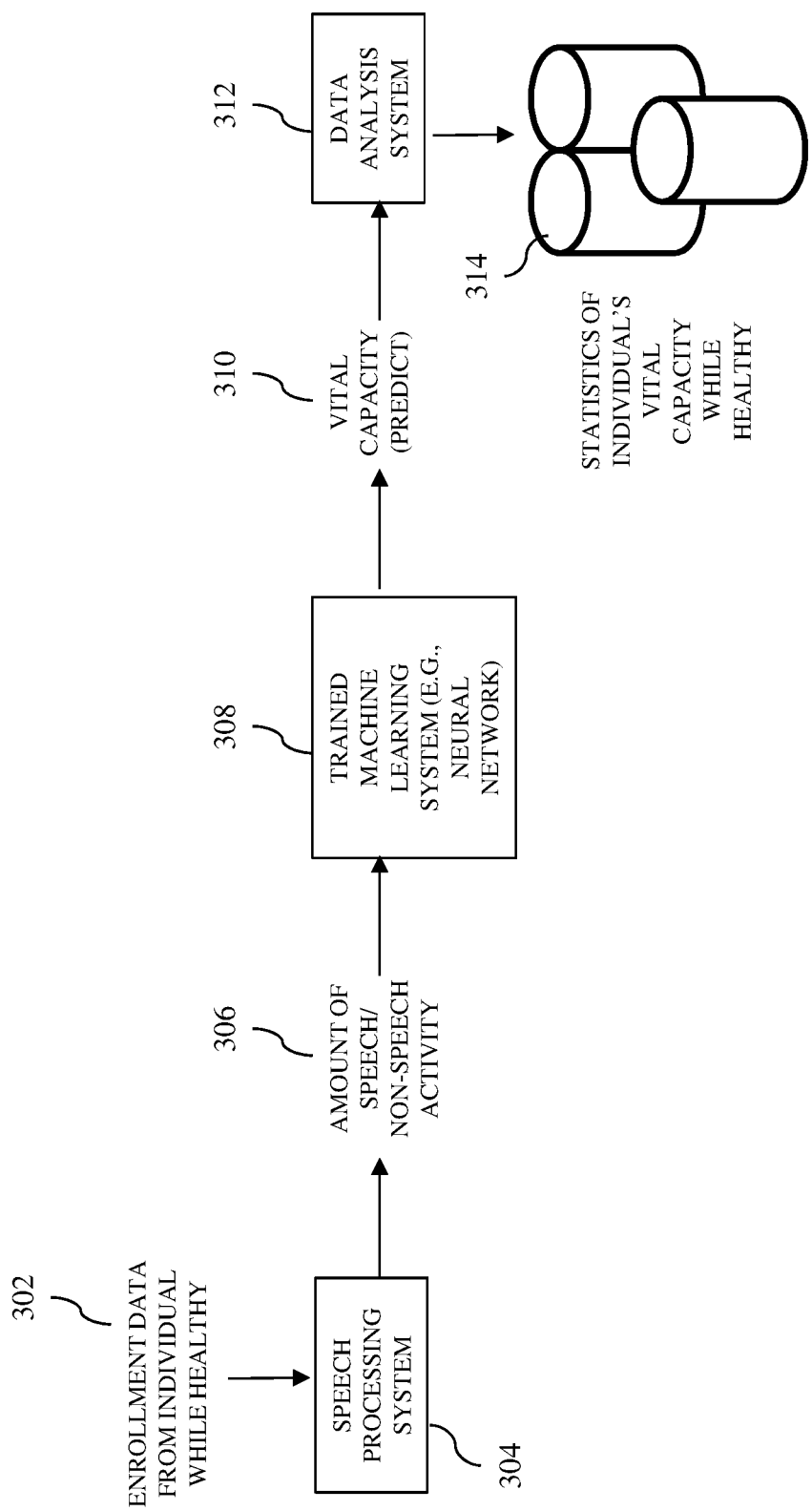
FIG. 3 illustrates an enrollment process for an individual in an embodiment.

FIG. 3 illustrates an enrollment process for an individual in an embodiment. The process customizes or determines a reference point or level for a specific individual for determining that particular individual's lung capacity. Speech data 302 from an individual is received. For example, the individual can be prompted to utter sounds such as the vowels, consonants, and/or other text and the sounds are captured. At 304, speech processing extracts or computes features or characteristics from the captured or received sounds. Extracted characteristics can include, but not limited to, amounts of speech/non-speech activity 306. At 308, a trained machine learning model, for example, a neural network model is run using the characteristics as input features for the machine learning model to predict lung capacity 310. For example, the machine learning model can be a neural network trained according to the process illustrated in FIG. 2. At 312, the predicted data (lung capacity) 310 can be designated as a baseline or a reference point for this individual. The predicted lung capacity can be stored, for example, in a database 314 or a storage device.

Figure 4:
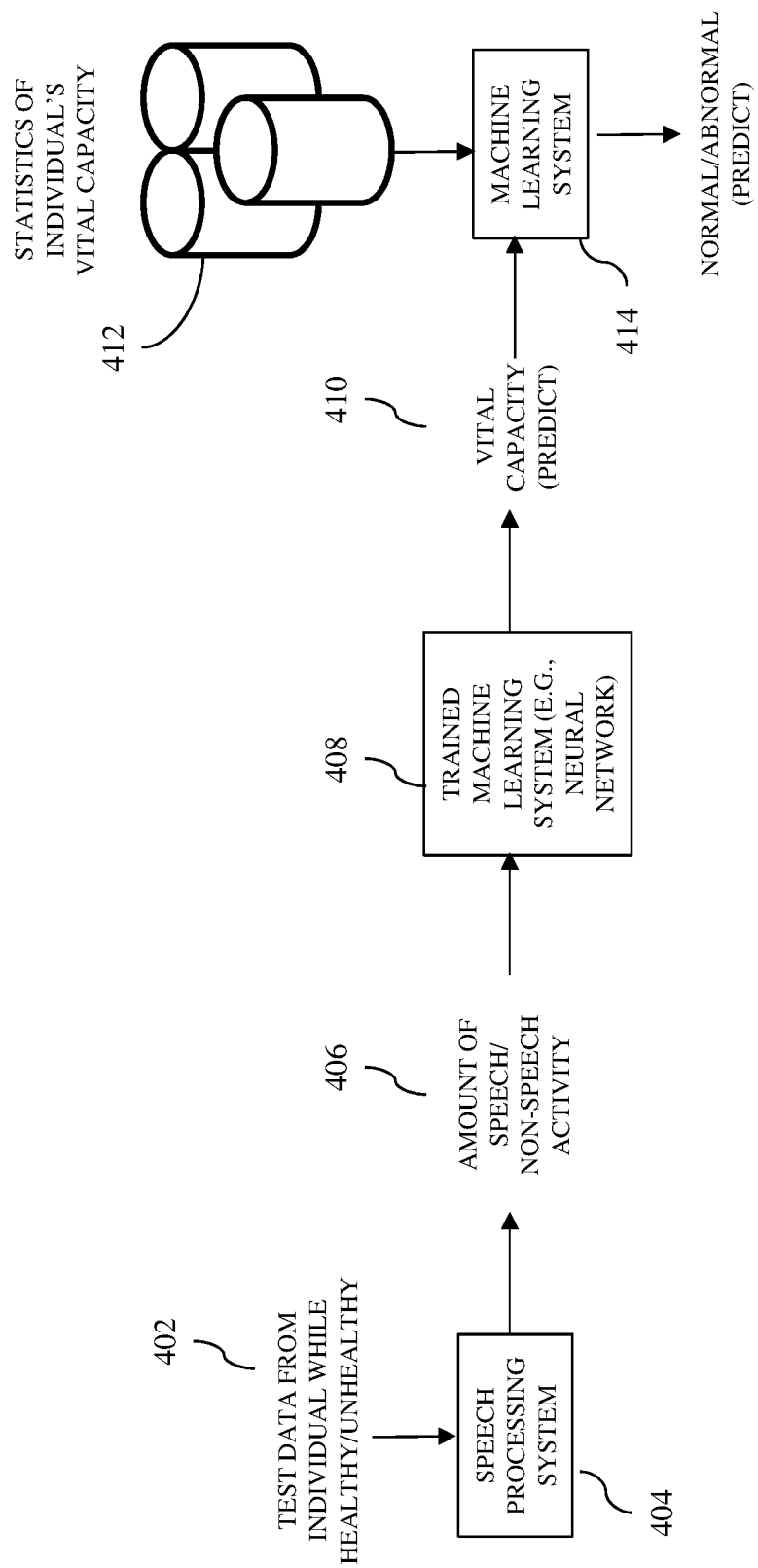
FIG. 4 illustrates performing of a test for an individual for detecting possible respiratory illness in an embodiment.

FIG. 4 illustrates performing of a test for an individual for detecting possible respiratory illness in an embodiment. Such test can be performed on a user's mobile device or another device, for example, running an application or app with user interface. Speech data 402 from an individual is received. For example, the individual can be prompted to utter sounds such as the vowels, consonants, and/or other text and the sounds are captured. At 404, speech processing extracts or computes features or characteristics from the captured or received sounds. Extracted characteristics can include, but not limited to, amounts of speech/non-speech activity 406. At 408, a trained machine learning model, for example, a neural network model is run using the characteristics as input features for the machine learning model to predict lung capacity 410. For example, the machine learning model can be a neural network trained according to the process illustrated in FIG. 2. At 414, the predicted data (lung capacity) 410 is compared with a baseline or a reference point, for example, previously stored (e.g., as shown in FIG. 3) and received or obtained from a database 412 storing the baseline for this use or individual. If the difference between the predicted lung capacity 410 and the baseline lung capacity exceeds or is outside a threshold (e.g., a predefined tolerance range), the processing at 414 flags or signals that the lung capacity of the user is deviating from the normal range.

Detecting amount of speech or non-speech activity (e.g., at 206 in FIG. 2, 306 in FIG. 3, and/or 406 in FIG. 4) can include the following. Speech is a sequence of consonants and vowels, nonharmonic and harmonic sounds with natural silences between them. This makes speech a complex signal with a broad range of spectro-temporal modulations. Useful temporal modulations of speech lie in the 0-20 Hz range, with a peak around 4 Hz. Spectral modulations, on the other hand, span a range between 0-6 cycle/octave. While pitch or voicing introduces modulations in the 2-6 cycle/octave range, modulations less than 2 cycle/octaves reflect formant information. Different kinds of acoustic features that capture information based on these modulation properties of speech can be used for effective speech/non-speech detection.

Figure 5:
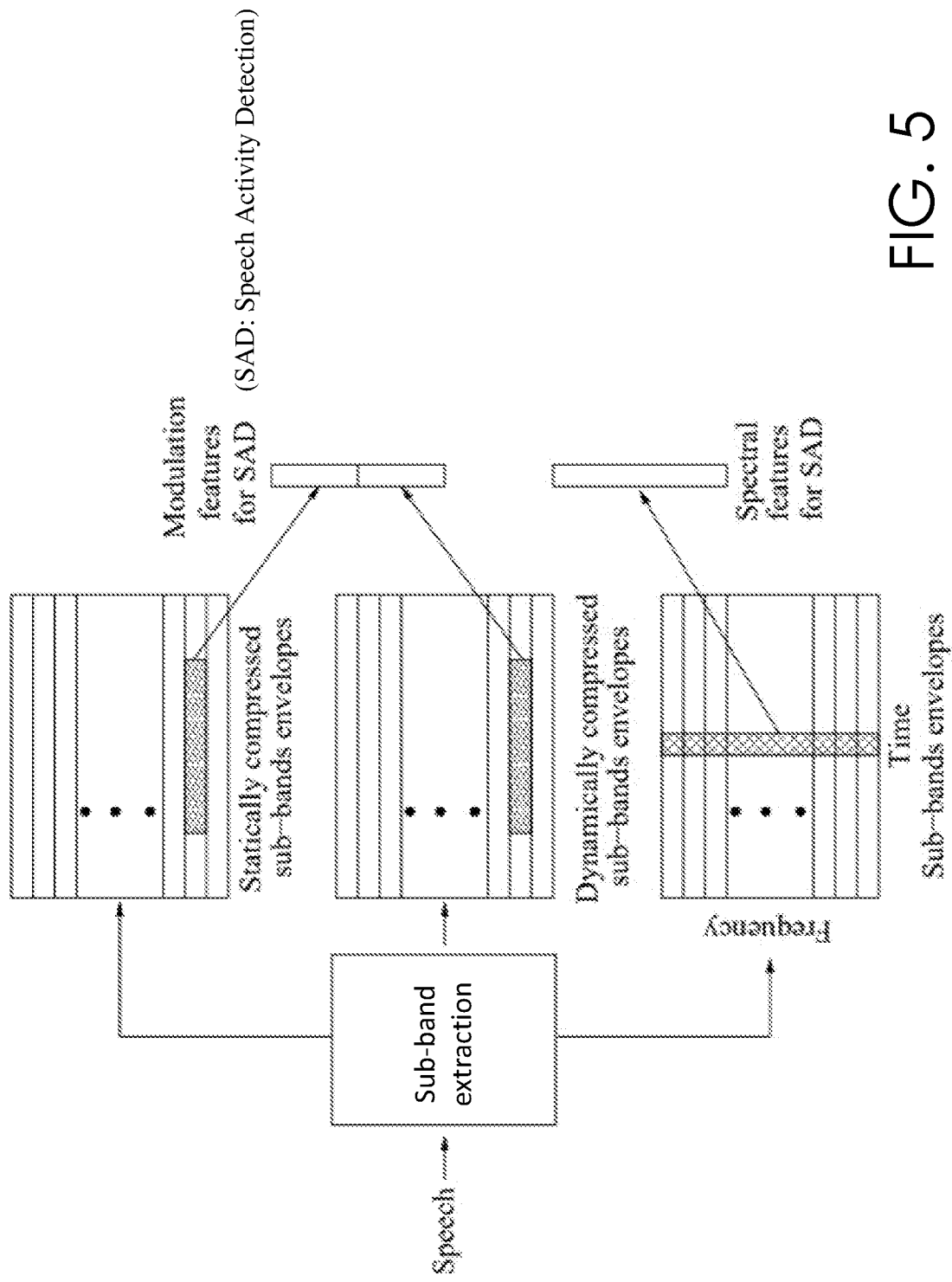
FIG. 5 illustrates spectral and modulation features for speech activity detection (SAD) in an embodiment.

FIG. 5 illustrates Spectral and modulation features for speech activity detection (SAD) in an embodiment. Acoustic features can be generated using different signal processing techniques and can be broadly categorized by the kinds of modulations they capture as short-term spectral features, long-term modulation frequency and joint spectro-temporal features. Short-term spectral features can be extracted from power spectral estimates in short analysis windows (e.g., 10-30 ms) of the speech signal, for example, Mel-frequency Cepstral Coefficients (MFCC), Perceptual Linear Prediction (PLP) features. Long-term modulation frequency components can be estimated in long analysis windows spanning few hundreds of milliseconds from sub-band envelopes of speech, for example, sub-band log-mel energy features with delta and double-delta features. Joint spectro-temporal features can be derived using 2D (2-dimensional) selective filters tuned to different rate and scales of the input spectrogram, for example, Multiresolution rate/scale features.

Figure 6:
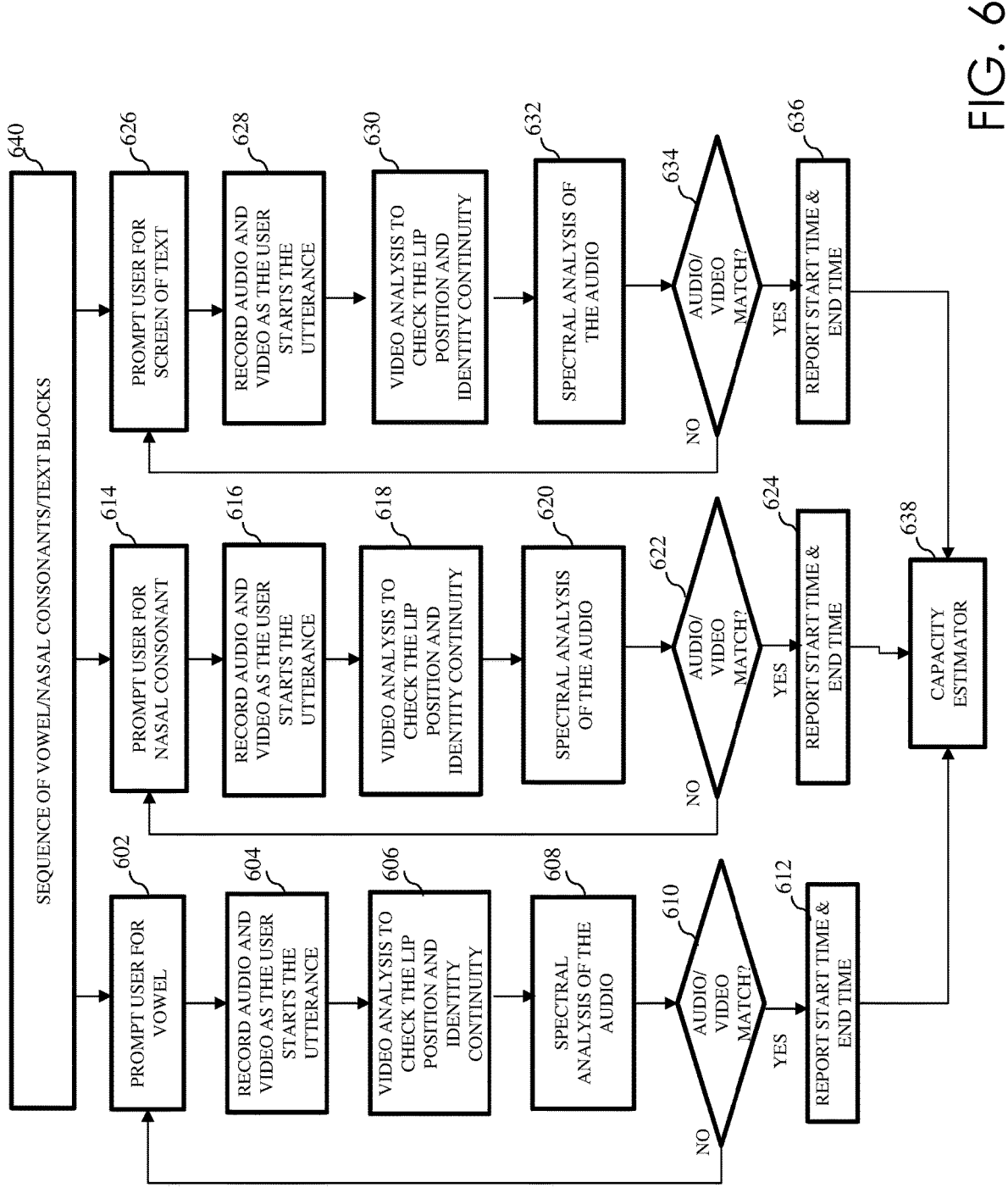
FIG. 6 illustrates a method of determining lung capacity in an embodiment.

FIG. 6 illustrates a method of determining lung capacity in an embodiment. One or more hardware processors, for example, running on a user device such as a mobile device, may perform the method. At 602, a user is prompted to utter a vowel sound or a sequence of vowel sounds. For example, the user may be prompted to make the sounds in a single exhalation. In an embodiment, the user may be presented with specific vowel or a sequence of vowels 640 to read out. At 604, video and audio as the user is uttering the sound are captured, for example, via a camera and microphone connected or coupled to the user's device.

At 606, analysis or image processing of the captured video can be performed. Such image processing verifies compliance with making the utterance, and can include, verifying the user's identity (e.g., the user for whom the lung capacity is being determined is the same user who is making the utterance), and verifying that the user is making the sound in a proper manner, for example, by analyzing the user's lip movement and/or posture while making the sound. At 608, spectral analysis of the captured audio can be performed, for example, to determine compliance related to making the sound, for instance, whether the user is rushing, making clipped sounds, making elongated sounds, mumbling, and/or whispering.

At 610, it is determined whether both video and audio are in compliance. If not, the process returns to 602, and the user is prompted again to make the sound. If both the video and the audio are in compliance, at 612, the start time and the end time of the utterance are recorded, and are transmitted together with the captured sound or utterance to a capacity estimator 638. The capacity estimator 638, for example, computes features or characteristics of the sound and determines lung capacity of the user, e.g., as shown in FIG. 4. The processing shown in FIG. 6 may also be used to collect proper utterance data for determining the user's baseline (e.g., shown in FIG. 3) and/or training a machine learning model (e.g., shown in FIG. 2).

The above processing can also be performed while the user is making other sounds, for example, consonant sound and reading a given text. For example, at 614, a user is prompted to utter a consonant or a sequence of consonants. For example, the user may be prompted to make the sounds in a single exhalation. In an embodiment, the user may be presented with specific consonant or a sequence of consonants 640 to read out. At 616, video and audio as the user is uttering the sound are captured, for example, via a camera and microphone connected or coupled to the user's device.

At 618, analysis or image processing of the captured video can be performed. Such image processing verifies compliance with making the utterance, and can include, verifying the user's identity (e.g., the user for whom the lung capacity is being determined is the same user who is making the utterance), and verifying that the user is making the sound in a proper manner, for example, by analyzing the user's lip movement and/or posture while making the sound. At 620, spectral analysis of the captured audio can be performed, for example, to determine compliance related to making the sound, for instance, whether the user is rushing, making clipped sounds, making elongated sounds, mumbling, and/or whispering.

At 622, it is determined whether both video and audio are in compliance. If not, the process returns to 614, and the user is prompted again to make the sound. If both the video and the audio are in compliance, at 624, the start time and the end time of the utterance are recorded, and are transmitted together with the captured sound or utterance to a capacity estimator 638. The capacity estimator 638, for example, computes features or characteristics of the sound and determines lung capacity of the user, e.g., as shown in FIG. 4.

Similarly, at 626, a user is prompted to utter a sound or sounds by reading a given text. For example, the user may be prompted to make the sounds in a single exhalation. In an embodiment, the user may be presented with specific text 640 to read out. At 628, video and audio as the user is uttering the sound are captured, for example, via a camera and microphone connected or coupled to the user's device.

At 630, analysis or image processing of the captured video can be performed. Such image processing verifies compliance with making the utterance, and can include, verifying the user's identity (e.g., the user for whom the lung capacity is being determined is the same user who is making the utterance), and verifying that the user is making the sound in a proper manner, for example, by analyzing the user's lip movement and/or posture while making the sound. At 632, spectral analysis of the captured audio can be performed, for example, to determine compliance related to making the sound, for instance, whether the user is rushing, making clipped sounds, making elongated sounds, mumbling, and/or whispering.

At 634, it is determined whether both video and audio are in compliance. If not, the process returns to 626, and the user is prompted again to make the sound. If both the video and the audio are in compliance, at 636, the start time and the end time of the utterance are recorded, and are transmitted together with the captured sound or utterance to a capacity estimator 638. The capacity estimator 638, for example, computes features or characteristics of the sound and determines lung capacity of the user, e.g., as shown in FIG. 4. The capacity estimator 638 may use all, or one or more of, or different combinations of the vowel sounds, consonant sounds, and text reading sounds 640, to determine lung capacity.

Figure 7:
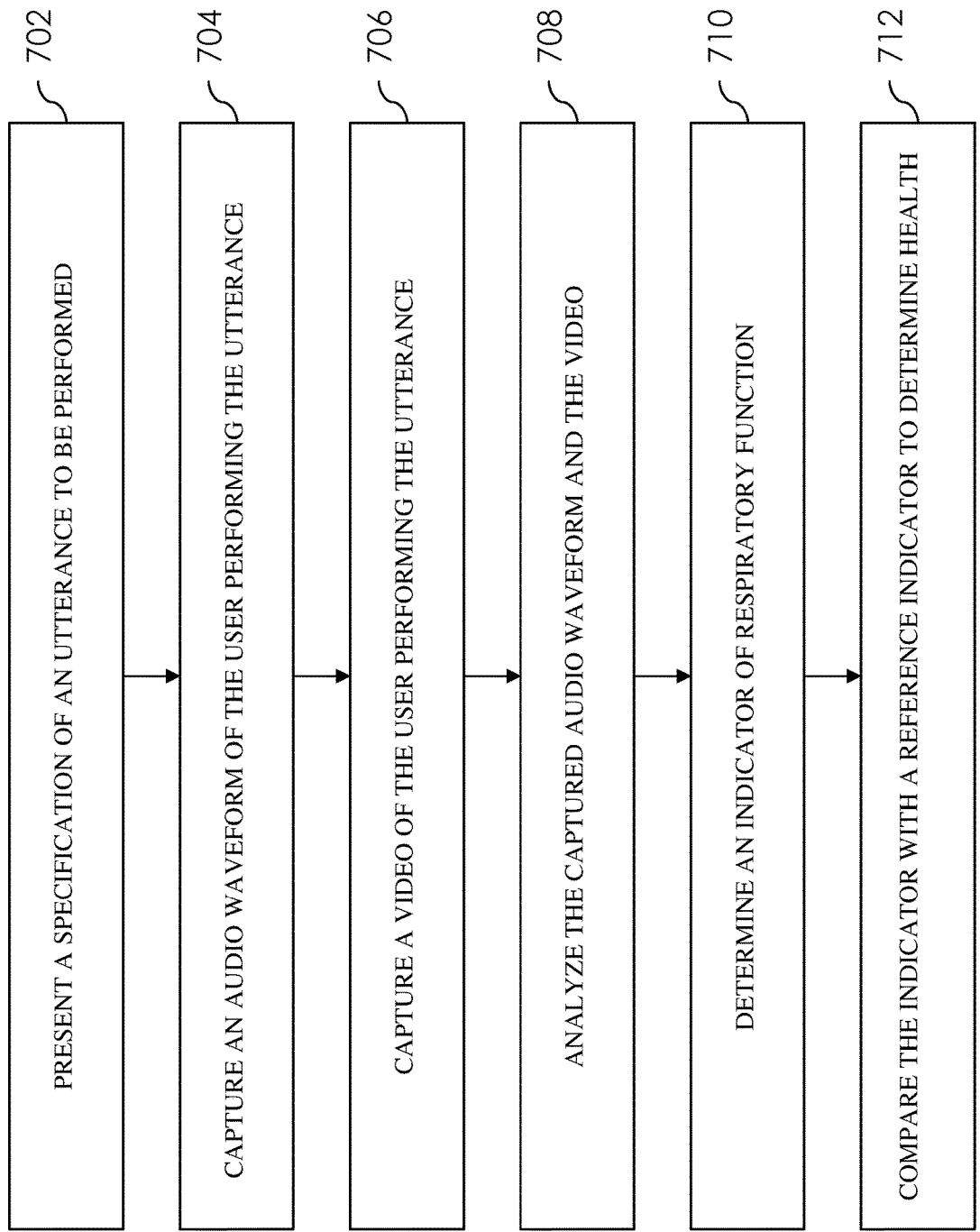
FIG. 7 is a diagram illustrating a method in an embodiment.

FIG. 7 is a diagram illustrating a method in an embodiment. The method can be performed by one or more hardware processors. At 702, a user can be presented with a specification of an utterance to be performed. The specification can include data to be uttered, e.g., a vowel sequence, a consonant sequence, text passage to read, a script to be read, a spoken passage to be repeated, a previously known song to be sung, and a sing-along video.

At 704, an audio waveform of the user performing the utterance is captured. For example, such audio waveform can be captured using a microphone or a like device coupled with or connected to a user device such as a mobile device. At 706, a video of the user performing the utterance is captured. For example, such video can be captured using a camera or a like device coupled with or connected to a user device such as a mobile device.

The performance of the utterance can be monitored for compliance with the specification. For example, at 708, the captured audio waveform and the video are analyzed for compliance with the specification. For instance, video analysis can determine whether the user making the utterance is the user for whom the lung capacity is being determined, whether the user is making proper or appropriate lip movements in order to produce proper sound characteristics for use in lung capacity measurement, whether the user is in a proper posture or position while making the utterance, and/or others. For example, the video data can be used to establish the continued identity of the user and/or to establish that the user uttered the prompted sequence correctly. Audio waveform can be analyzed to determine whether the user is too rushing in making the utterance, whether the syllables are being uttered properly (e.g., not clipped, not too elongated, etc.), and/or others. For example, the captured information can be compared with threshold values or standard values, which can be predefined, for determining compliance.

At 710, based on the audio waveform, an indicator of respiratory function can be determined. For instance, the indicator can be lung capacity measurement. In an embodiment, a neural network trained to predict the lung capacity can be run using the characteristics of the audio waveform as input features, for example, as described above with reference to FIGS. 2, 3 and 4. Input features can include spectral and/or temporal features associated with the utterance. For example, an input feature can be the length of time it takes the user to perform a portion of the utterance on a single breath.

At 712, the indicator can be compared with a reference indicator to determine health of the user, for example, as described above with reference to FIGS. 3 and 4. In another aspect, an indicator can be the length of time it takes the user to perform a portion of the utterance on a single breath. Such an indicator can be compared with a user's baseline measurement of time it takes the user to perform the same utterance while the user is considered to be in a healthy condition. The reference indicator includes data associated with the user acquired during a period in which the user is considered healthy. For example, the reference indicator can be constructed by combining a plurality of sessions performed by the user. In another embodiment, the reference indicator can include data associated with a group of individuals in the user's demographic group, or a group having similar physical characteristics as the user.

In an embodiment, one or more processing of the method, for example, the analyzing, determining and comparing can be performed on a remote device over a computer network, for example, on a cloud system, for example, using the audio and/or video information collected from the user via a user's mobile device, which may be running an app or an application programming interface (API).

Figure 8:
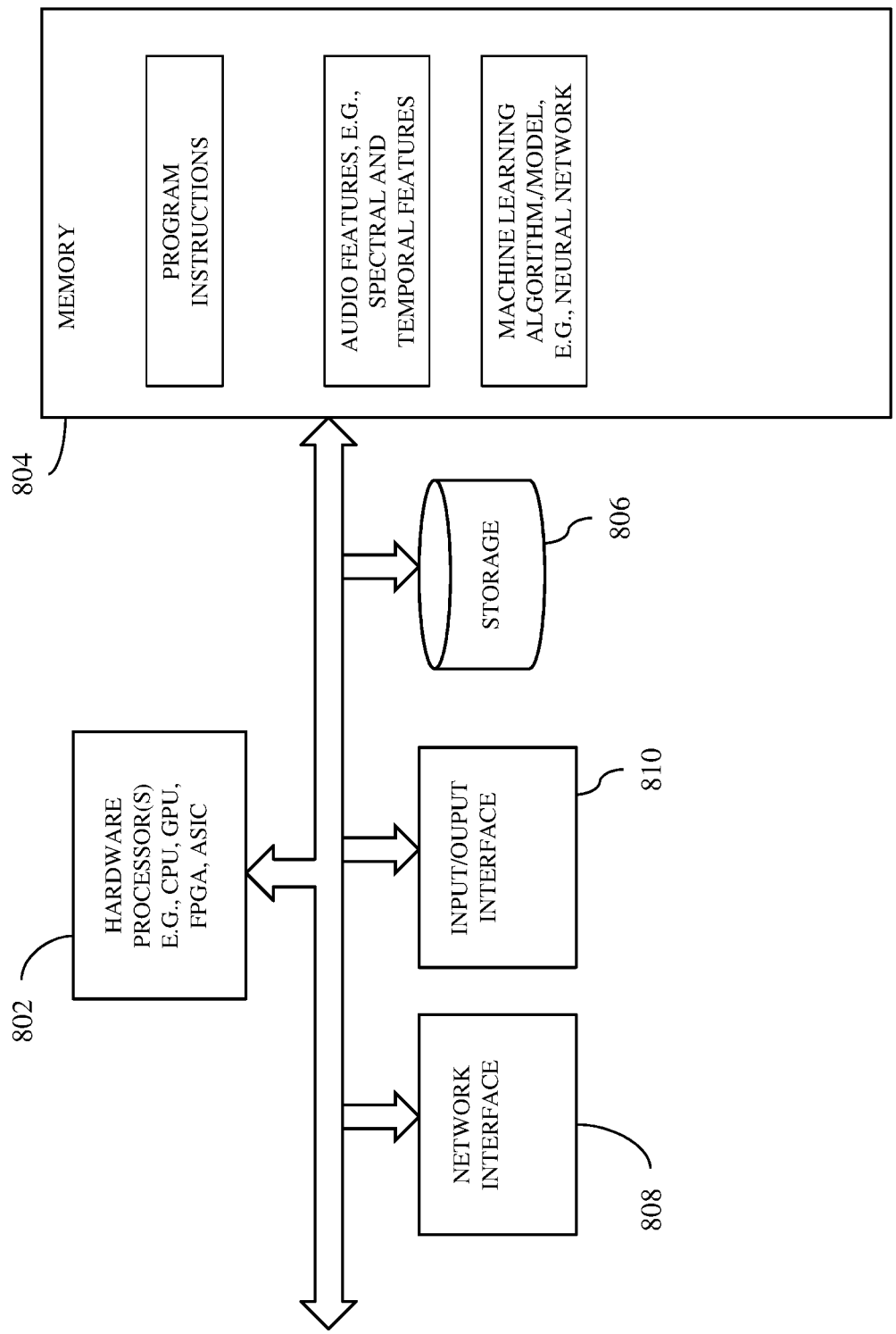
FIG. 8 is a diagram showing components of a system in one embodiment that determines lung capacity of a user.

FIG. 8 is a diagram showing components of a system in one embodiment that determines lung capacity of a user, for example, allows a user to perform self-assessment of the user's lung capacity. One or more hardware processors 802 such as a central processing unit (CPU), a graphic process unit (GPU), and/or a Field Programmable Gate Array (FPGA), an application specific integrated circuit (ASIC), and/or another processor, may be coupled with a memory device 804, and cause presenting to a user a specification of an utterance to be performed, capturing an audio waveform of the user performing the utterance, and capturing a video of the user performing the utterance. One or more hardware processors 802 may analyze the captured audio waveform and the video for compliance with the specification, and based on the audio waveform, determine an indicator of respiratory function. One or more hardware processors 802 may compare the indicator with a reference indicator to determine health of the user. A memory device 804 may include random access memory (RAM), read-only memory (ROM) or another memory device, and may store data and/or processor instructions for implementing various functionalities associated with the methods and/or systems described herein. One or more processors 802 may execute computer instructions stored in memory 804 or received from another computer device or medium. A memory device 804 may, for example, store instructions and/or data for functioning of one or more hardware processors 802, and may include an operating system and other program of instructions and/or data. One or more hardware processors 802 may receive input comprising user utterance and/or video of the user making utterance. One or more hardware processors 802 may generate a prediction model that predicts lung capacity. The prediction model can also be used to determine a baseline or reference point for the user or a group of users, for example, for comparison. Input data and/or a prediction model may be stored in a storage device 806 or received via a network interface 808 from a remote device, and may be temporarily loaded into a memory device 804 for use. One or more hardware processors 802 may be coupled with interface devices such as a network interface 808 for communicating with remote systems, for example, via a network, and an input/output interface 810 for communicating with input and/or output devices such as a keyboard, mouse, display, and/or others.

Figure 9:
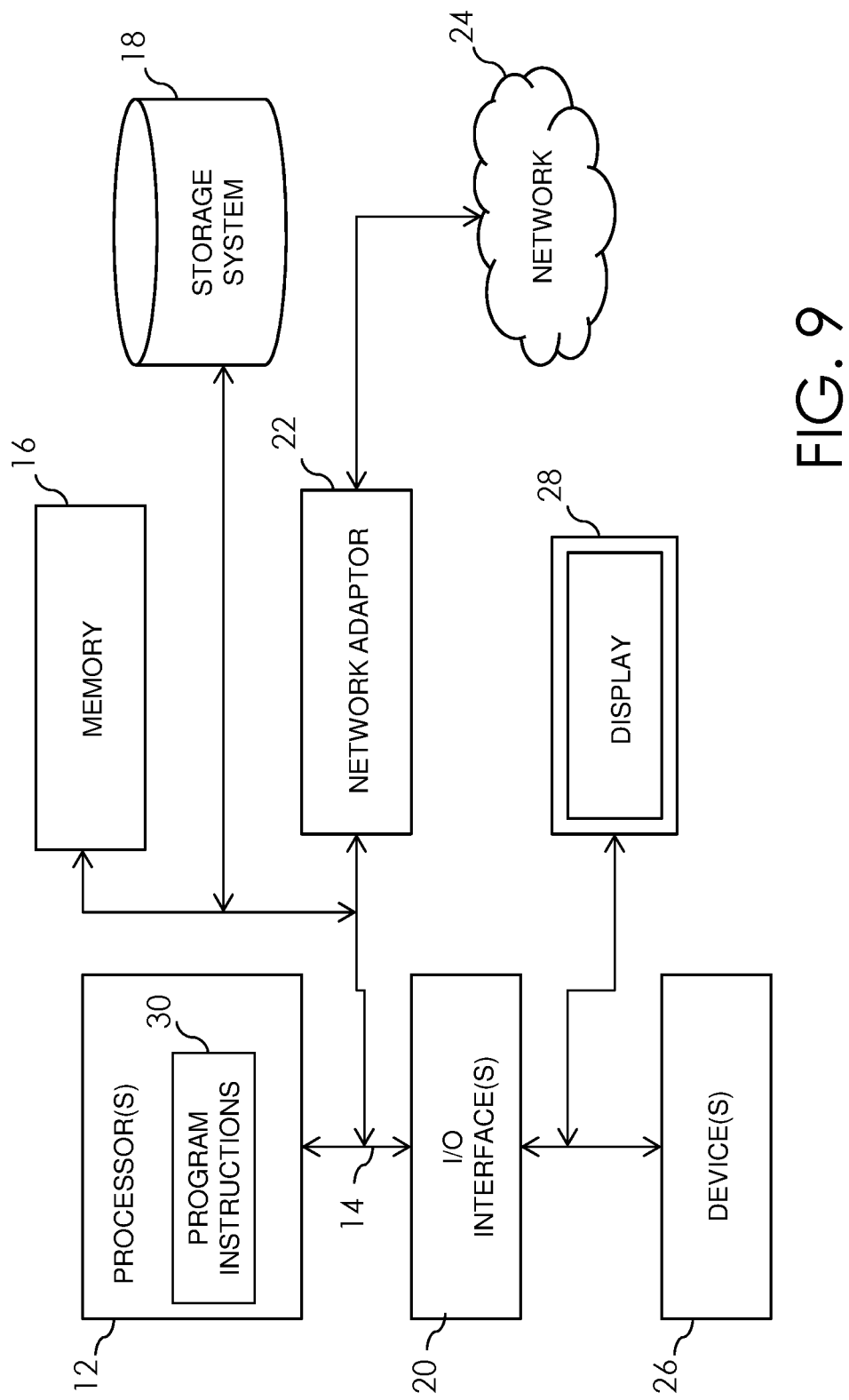
FIG. 9 illustrates a schematic of an example computer or processing system that may implement a system in an embodiment.

FIG. 9 illustrates a schematic of an example computer or processing system that may implement a system in an embodiment. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 9 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being run by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

It is understood in advance that although this disclosure may include a description on cloud computing, implementation of the teachings recited herein are not limited to a cloud computing environment. Rather, embodiments of the present invention are capable of being implemented in conjunction with any other type of computing environment now known or later developed. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 10:
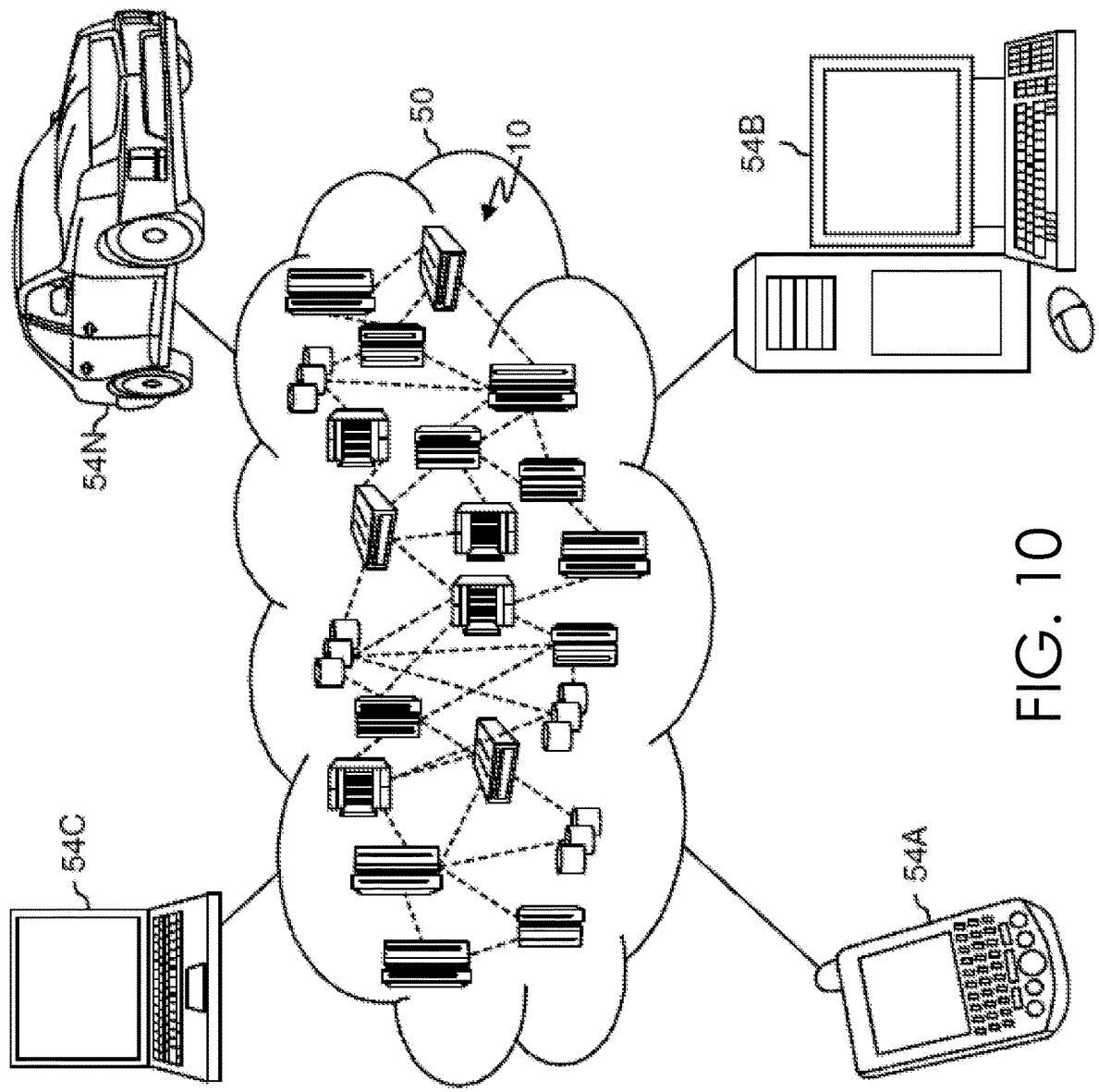
FIG. 10 illustrates a cloud computing environment in one embodiment.

Referring now to FIG. 10, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Figure 11:
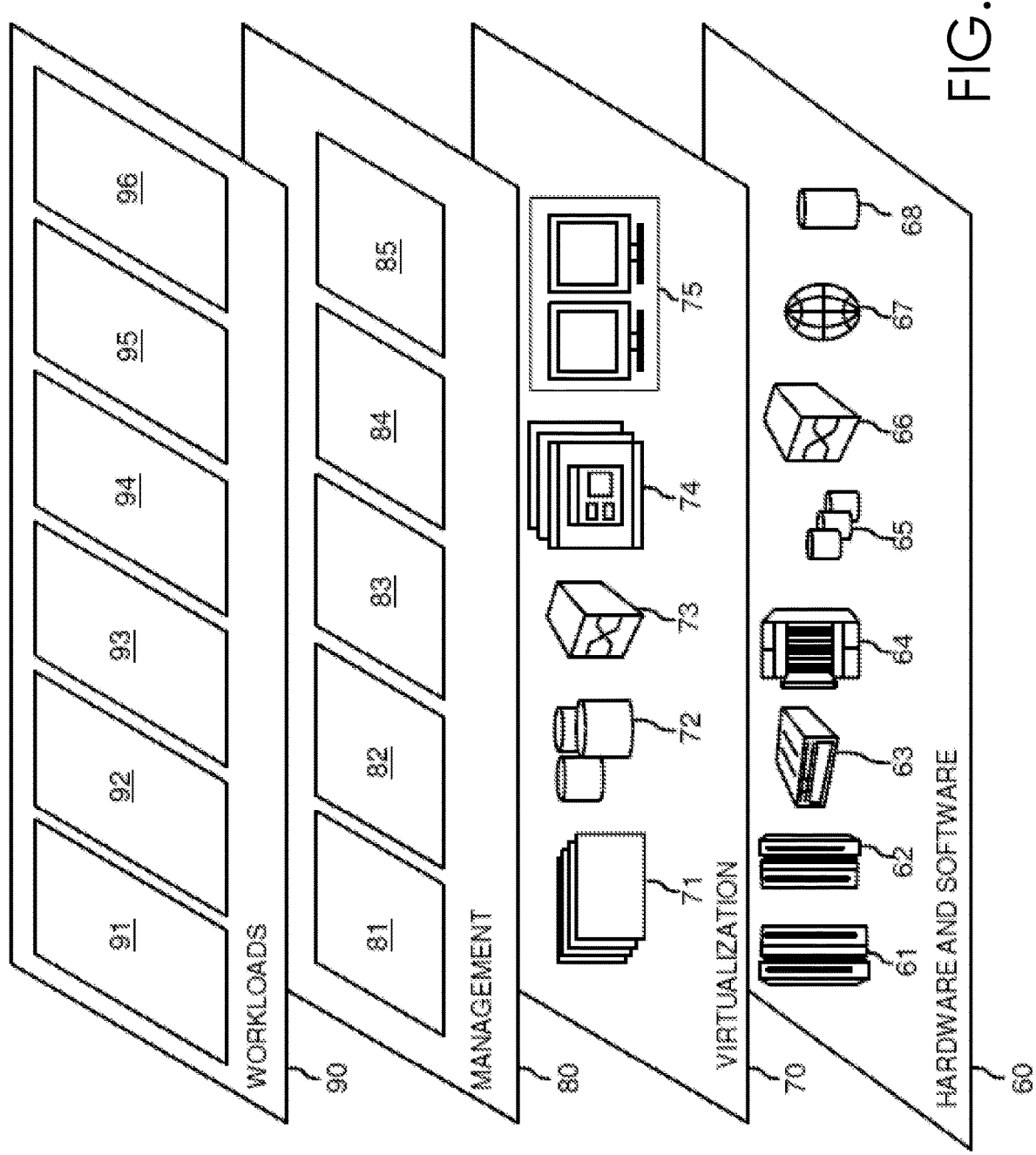
FIG. 11 illustrates a set of functional abstraction layers provided by cloud computing environment in one embodiment.

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below.

Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and speech, lung capacity processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, run concurrently, substantially concurrently, in a partially or wholly temporally overlapping manner, or the blocks may sometimes be run in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having," when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
   presenting to a user a specification of an utterance to be performed;
   capturing an audio waveform of the user performing the utterance;
   capturing a video of the user performing the utterance;
   analyzing the captured audio waveform and the video for compliance with the specification, wherein analyzing includes at least extracting spectral features, modulation frequency and joint spectro-temporal features from the captured audio waveform, the captured video further being analyzed using image processing to establish continued identity of the user performing the utterance;
   determining an indicator of respiratory function based on at least the extracted spectral features, modulation frequency and joint spectro-temporal features; and
   comparing the indicator with a reference indicator to determine health of the user, the reference indicator including a baseline model calibrated based on user's repeated utterances of a given sound pattern over time,
   wherein the determining an indicator of respiratory function includes running a machine learning model trained to predict lung capacity using input features computed from at least the extracted spectral features, modulation frequency and joint spectro-temporal features.

2. The method of claim 1, wherein the indicator includes the length of time it takes the user to perform a portion of the utterance on a single breath.

3. The method of claim 1, wherein at least the presenting and the capturing are performed using a mobile device.

4. The method of claim 1, wherein the specification of the utterance includes at least one of: a script to be read, a spoken passage to be repeated, a previously known song to be sung, and a sing-along video.

5. The method of claim 1, wherein the reference indicator includes data associated with the user acquired during a period in which the user is considered healthy.

6. The method of claim 1, wherein the reference indicator is constructed by combining a plurality of sessions performed by the user.

7. The method of claim 1, wherein the reference indicator includes data associated with a group of individuals in the user's demographic group.

8. The method of claim 1, wherein the analyzing, determining and comparing are performed on a remote device over a computer network.

9. The method of claim 1, further including establishing that the user uttered the utterance in the specification correctly using the captured video.

10. A system comprising:
    a processor; and
    a memory coupled with the processor;
    the processor configured to:
      present to a user a specification of an utterance to be performed;
      capture an audio waveform of the user performing the utterance;
      capture a video of the user performing the utterance;
      analyze the captured audio waveform and the video for compliance with the specification, wherein the processor is configured to analyze the captured audio waveform at least by extracting spectral features, modulation frequency and joint spectro-temporal features from the captured audio waveform, the captured video further being analyzed using image processing to establish continued identity of the user performing the utterance;
      determine an indicator of respiratory function based on at least the extracted spectral features, modulation frequency and joint spectro-temporal features; and
      compare the indicator with a reference indicator to determine health of the user, the reference indicator including a baseline model calibrated based on user's repeated utterances of a given sound pattern over time,
      wherein the processor is configured to determine an indicator of respiratory function at least by running a machine learning model trained to predict lung capacity using input features computed from at least the extracted spectral features, modulation frequency and joint spectro-temporal features.

11. The system of claim 10, wherein the indicator includes the length of time it takes the user to perform a portion of the utterance on a single breath.

12. The system of claim 10, wherein the specification of the utterance includes at least one of: a script to be read, a spoken passage to be repeated, a previously known song to be sung, and a sing-along video.

13. The system of claim 10, wherein the reference indicator includes data associated with the user acquired during a period in which the user is considered healthy.

14. The system of claim 10, wherein the reference indicator is constructed by combining a plurality of sessions performed by the user.

15. The system of claim 10, wherein the reference indicator includes data associated with a group of individuals in the user's demographic group.

16. A computer program product comprising a computer readable storage medium having program instructions embodied therewith, the program instructions readable by a device to cause the device to:

present to a user a specification of an utterance to be performed;
capture an audio waveform of the user performing the utterance;
capture a video of the user performing the utterance;
analyze the captured audio waveform and the video for compliance with the specification, wherein the device is caused to analyze the captured audio waveform at least by extracting spectral features, modulation frequency and joint spectro-temporal features from the captured audio waveform, the captured video further being analyzed using image processing to establish continued identity of the user performing the utterance;
determine an indicator of respiratory function based on at least the extracted spectral features, modulation frequency and joint spectro-temporal features; and
compare the indicator with a reference indicator to determine health of the user, the reference indicator including a baseline model calibrated based on user's repeated utterances of a given sound pattern over time,
wherein the device is caused to determine an indicator of respiratory function at least by running a machine learning model trained to predict lung capacity using input features computed from at least the extracted spectral features, modulation frequency and joint spectro-temporal features.

* * * * *